United States Patent [19]

Wozniak

[11] Patent Number: 4,470,415
[45] Date of Patent: Sep. 11, 1984

[54] SUTURELESS VASCULAR ANASTOMOSIS MEANS AND METHOD

[75] Inventor: John J. Wozniak, Columbia, Md.

[73] Assignee: The Johns Hopkins University, Baltimore, Md.

[21] Appl. No.: 409,367

[22] Filed: Aug. 19, 1982

[51] Int. Cl.³ .............................................. A61B 17/04
[52] U.S. Cl. ........................... 128/334 R; 128/334 C; 29/447; 29/DIG. 35
[58] Field of Search ...................... 128/334 C, 334 R; 604/405, 408–410, 262; 29/DIG. 35, 447

[56] References Cited

U.S. PATENT DOCUMENTS

| 1,151,300 | 8/1915 | Soresi | 128/334 C |
| 3,316,914 | 5/1967 | Collito | 128/334 C |
| 3,606,888 | 9/1971 | Wilkinson | 128/334 C |
| 3,774,615 | 11/1973 | Lim et al. | 128/334 C |
| 3,781,969 | 1/1974 | Anderson | 29/447 |
| 3,800,403 | 4/1974 | Anderson et al. | 29/447 |
| 3,908,662 | 9/1975 | Razgulov et al. | 128/334 C |
| 4,169,477 | 10/1979 | Bokros | 128/334 R |
| 4,379,009 | 4/1983 | Shibata et al. | 29/447 |

Primary Examiner—C. Fred Rosenbaum
Assistant Examiner—Gene B. Kartchner
Attorney, Agent, or Firm—Robert E. Archibald; H. Donald Nelson

[57] ABSTRACT

A means and method for sutureless surgical anastomosis. A heat shrinkable sleeve is placed around two tubular members to be anastomosed and then shrunk to engage and maintain the two tubular members in an anastomotic relationship. The ends of the tubular members are everted over rigid or semi-rigid ferrules placed on the ends of the tubular members.

54 Claims, 30 Drawing Figures

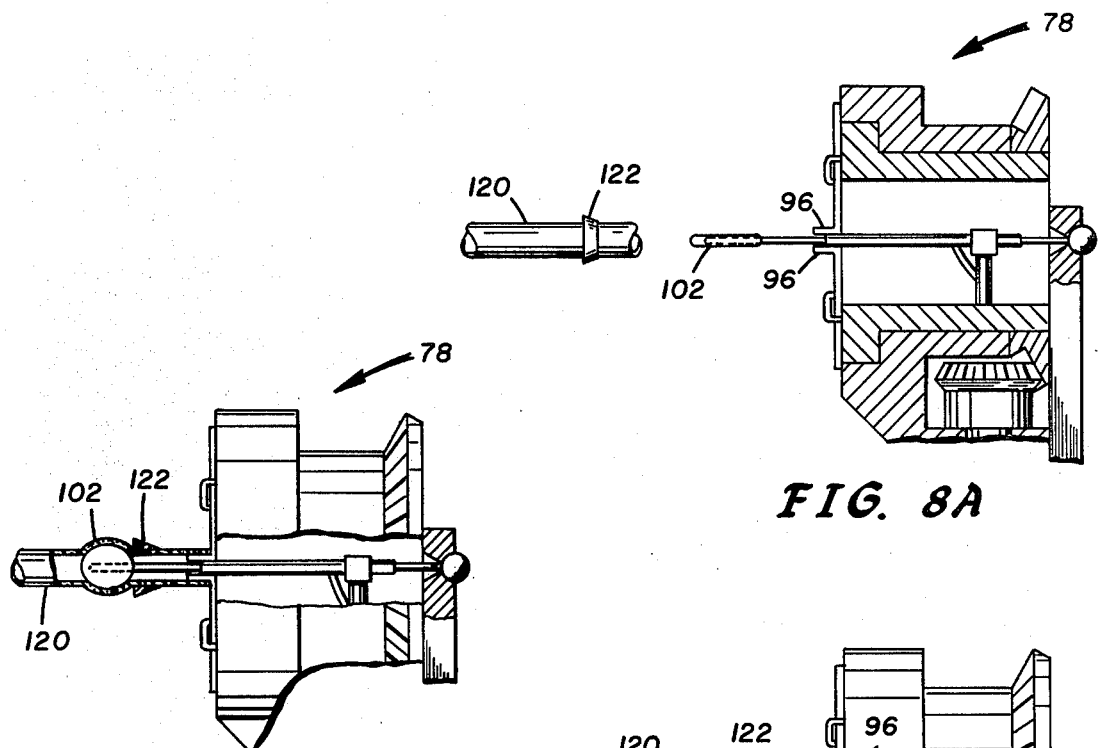
FIG. 8A
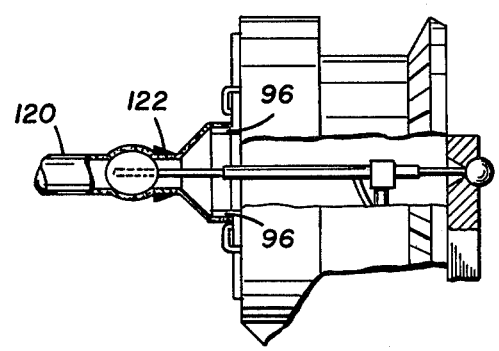
FIG. 8C
FIG. 8B
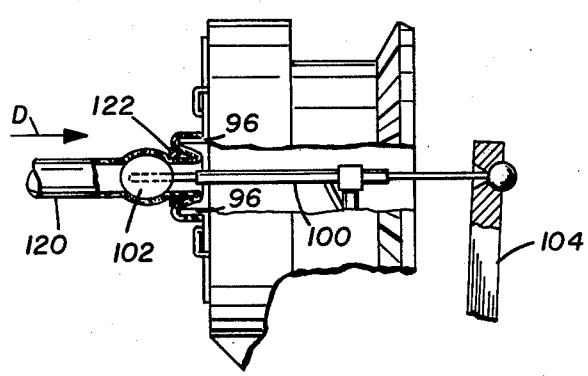
FIG. 8D
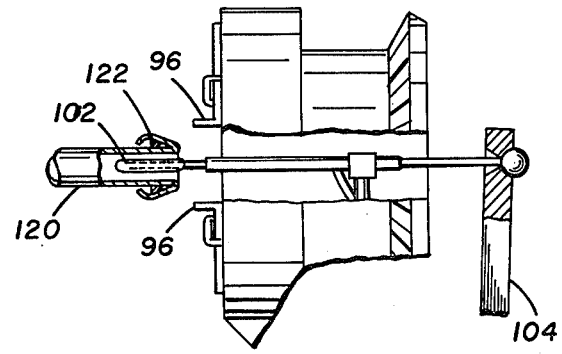
FIG. 8E

SUTURELESS VASCULAR ANASTOMOSIS MEANS AND METHOD

STATEMENT OF GOVERNMENTAL INTEREST

The Government has rights in this invention pursuant to Contract No. N00024-81-C-5301 awarded by the Department of the Navy.

BACKGROUND OF THE INVENTION

This invention relates generally to a means and method for surgical anastomosis and more specifically to a means and method for performing sutureless surgical end-to-end anastomosis.

Severed blood vessels and other tubular fluid carrying body members requiring anastomosis are frequently encountered in penetrating wounds inflicted during combat, civil violence and automobile accidents. Other surgical procedures requiring anastomosis are the by-passing of blocked tubular members or replacement of a portion of a vessel or other tubular member with a portion of a vessel taken from another part of the body. Still another surgical procedure requiring anastomosis is the replacement of a damaged or diseased vessel or other tubular member with a prosthesis. At the present time, when these types of surgical procedures are necessary and when the requisite skills and facilities are available, the tubular members are anastomosed using a suturing procedure. As can be appreciated, the suturing of blood vessels or other tubular members requires exquisite skill and is a time consuming procedure. Under combat or emergency conditions, the requisite skills, facilities and time may not be available to prevent loss of limb or life.

The difficulties associated with anastomotic procedures are illustrated by examining the problems associated with vascular anastomosis. Arteries within man have three coats: the outer coat or tunica adventitia, consisting of a strong fibrous sheath; the middle coat or tunica media, consisting of muscular fibers; and the inner coat or tunica intima, consisting of a layer of elastic tissue lined with plate-like endothelial cells. When an artery is severed the muscular coat instantly contracts, drawing the cut end within the outer fibrous sheath so that a very small hole is left to be closed by blood clotting. Because of the constrictive response of the tunica media, a small artery usually can be severed without hemorrhaging. However, the same response may tend to inhibit reestablishment of patency if the vessel is rejoined.

The suturing process, in an anastomotic procedure, must be conducted by a surgeon specially trained in vascular surgery. Using a curved needle the sutures must be placed precisely, piercing the tunica adventitia from the outside and the tunica intima from the inside in the exact locations for proper vessel approximation (tunica intima aligned and in good contact). Either individual or a continuous running suture are used. The suturing procedure, as can be appreciated, is an extremely time consuming process. For small vascular members, the suturing procedure must be conducted under magnification by a surgeon trained in microvascular anastomosis. Typically, for an artery with a 3 mm lumen approximately 20 stitches must be taken around the circumference using a 6-0 (0.1 mm diameter) thread. It is usually not technically possible to perform a microvascular anastomosis in less than 30 minutes. Because of the time required for the anastomotic suturing procedure, the greatest success rate is achieved when anastomosis is performed in areas having a good collateral blood supply or in an area which can tolerate the loss of blood flow for the time required for the anastomotic suturing procedure. Inordinate time and skill is required to insure that the tunica intima of the two vessels being anastomosed are joined in intimate contact to prevent vascular occlusion and to insure proper healing of the vessel. A vascular occlusion at the site of anastomosis can lead to disastrous results including loss of life or limb.

Another problem area which is illustrative of the problem associated with sutures in an anastomotic procedure is intracranial surgery and the difficulties presented by the application of sutures to anastomose intracranial vessels. Cerebral arteries as compared to extracerebral vessels have less tunica adventitia, reduced tunica media and have many perforating branches which preclude the surgeon from rotating the vessel during the anastomotic suturing procedure. The limited time that intracranial vessels can be occluded without brain damage hamper and sometimes preclude the successful application of sutures to cerebral vessels.

Still another problem area which is further illustrative of the problem associated with sutures is the procedure of grafting a prosthesis to an existing vessel. It has been found that the clinical success of prosthetic grafts is dependent, to a large extent, on the suturing procedure. In other words, the suturing procedure is a major cause of failure of prosthetic grafts. The sutures must be properly made to avoid interfaces which cause tubulent flow and clotting. If the sutures are too tight or too closely spaced they produce necrotic areas. If the sutures are too loose or too far apart leakage occurs and early failure occurs. Additionally, it has been found that a strong fibrous bond does not develop between the graft and the vessel so that the union is dependent on the strength of the anastomotic suture. Because of the inherently weak junction coupled with fraying of the prostheses caused to a large part by the sutures, false aneurysms have been the cause of complications. This problem is aggravated when the conditions of the vessel are such that its ability to maintain sutures is impaired by degenerative disease. As a result, a number of techniques have been investigated to reinforce the suture line such as suturing reinforcing sleeves over the vessel-to-prosthetic junction. Furthermore, prostheses, depending on the type of material and the type of weave or knit, vary in their ability to hold sutures.

The prior art discloses a number of attempts to develop a sutureless technique to perform anastomosis. One method has employed tissue adhesives. Animal research, however, has shown that adhesive techniques are not satisfactory and often result in necrosis of the tunica media at the site of the junction, thrombosis, if any adhesive enters the lumen, and a high incidence of early hemorrhaging, "Handbook of Biomedical Plastics", Lee, Henry and Neville, Kris, Pasadena Technology Press, pages 4-14.

Other attempts to develop a successful sutureless anastomotic technique are represented by U.S. Pat. Nos. 3,221,746, 3,357,432, 3,648,295, 3,683,926 and 4,267,842. However, all of these feature an inner tube-like device placed inside the vessels to be anastomosed. As is known in the art, a constriction, irregularity or foreign material within the lumen of a blood vessel tends to cause a blood clot to form which may eventually occlude the vessel.

Still other attempts to develop a successful sutureless anastomotic technique are represented by U.S. Pat. Nos. 3,316,914, 3,774,615, 4,214,586 and 4,233,981. U.S. Pat. Nos. 3,316,914 and 4,233,981 both feature a pair of annular flanges. Pointed pins on one of the flanges are pierced through the vessel walls and are inserted into apertures in the other flange to hold and locate the vessel walls. The flanges in U.S. Pat. No. 4,233,981 are held in place by nuts and bolts. The flanges in U.S. Pat. No. 3,316,914 are held in place by sutures threaded through aligned holes on the flanges.

U.S. Pat. No. 3,774,615 discloses a device comprising a connecting ring over which the ends of the severed vessel are pulled and a fastening means to secure the severed vessel ends to the connecting ring. U.S. Pat. No. 4,214,586 discloses a three-piece coupling device comprising two open bore cylindrical adaptors and an open bore cylindrical connector. Each end of the vessel to be anastomosed are passed through the axial bore of an adaptor and everted over the end of the adaptor. The adaptors are then inserted into opposite ends of the connector until the everted ends of the vessel abut under light compression. Means integral to the adaptors and connector secure the device in place.

Other methods, including stapling, have been suggested to avoid the disadvantages of suturing. However, each of the proposed methods either have a complicated mechanical device that may be unadaptable in certain surgical situations, have a portion of the device within the vessel lumen or damage the vascular wall.

The ideal anastomotic technique should provide firm intimate contact between the inner coats of the members being anastomosed to prevent leakage while promoting healing, should not damage the vascular wall to prevent necrosis and a source of infection, should be completely external to the vascular lumen to prevent thrombi from forming, should provide fast and simple execution, should be able to be accomplished without rotation of the vessel or member being anastomosed, should require a lesser degree of skill than now required of vascular surgeons, on the part of the surgeon performing the anastomosis and should be able to be performed in a combat or emergency situation.

It is therefore one object of this invention to provide a sutureless anastomosis technique that is rapid, simple and that can be performed in a combat or emergency situation.

It is another object of this invention to provide a sutureless anastomosis technique that provides perfect adaptation of the members being anastomosed without damage to the walls of the members.

It is a further object of this invention to provide a sutureless anastomosis technique that is reliable and requires less skill on the part of a surgeon than anastomotic suturing and which can be performed in a combat or emergency situation.

It is still another object of this invention to provide a sutureless anastomosis technique that does not require the members being anastomosed to be rotated.

It is still a further object of this invention to provide a sutureless anastomosis technique that does not require any foreign object within the lumen of the members being anastomosed.

It is also another object of this invention to provide a sutureless anastomosis technique that is applicable to prosthetic grafts.

Other objects, advantages and novel features of the present invention will become apparent from the following detailed description of the invention when considered in conjunction with the accompanying drawings.

BRIEF DESCRIPTION OF THE DRAWINGS

The above and further objects and novel features of the invention will more fully appear from the following description when the same is read in connection with the accompanying drawings. It is to be understood, however, that the drawings are for the purpose of illustration only, and are not intended as a definition of the limits of the invention.

FIGS. 8A–8E are sequential pictorials of the method of everting each of the ends of the two members being anastomosed over the ferrule placed on each of the ends.

DESCRIPTION OF THE PREFERRED EMBODIMENT

Figure 1A:
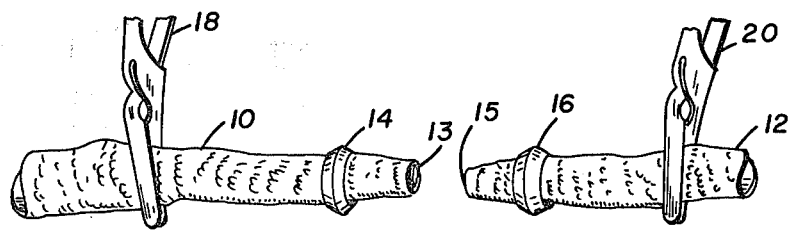
FIGS. 1A–1D are sequential pictorials of the anastomosis technique taught by the present invention.

Referring now to the drawings wherein like numerals indicate like elements, FIGS. 1A–1D are sequential pictorials of the anastomotic technique as taught by the present invention. FIG. 1A shows a first member 10 and a second member 12 which are to be anastomosed. A first ferrule 14 is placed over end 13 of first member 10. A second ferrule 16 is placed over end 15 of second member 16. Clamps 18, 20 are employed by a surgeon to stop the flow of fluid through members 10, 12 and to hold members 10, 12 in place during the anastomosis procedure. The anastomosis technique taught by the present invention is intended to be employed for any tubular member or organ including, but not limited to, veins, arteries, oviducts, urethras, phrynxes, intestines, ductus deferens, nerves, fallopian tubes, etc. In addition, the anastomosis procedure taught by the present invention is intended to be employed when one of the members is a replacement vessel taken from another part of the body or is a prosthesis.

The ferrules 14, 16 are selected to have an inner diameter approximately the same as the outer diameter of the vessel being anastomosed. Whenever a blood vessel is being anastomosed it may be preferred to have ferrules 14, 16 slightly larger than the vessel being anastomosed to preclude the anastomosed vessel having a constriction therein which may cause a thrombus to form.

Figure 1B:
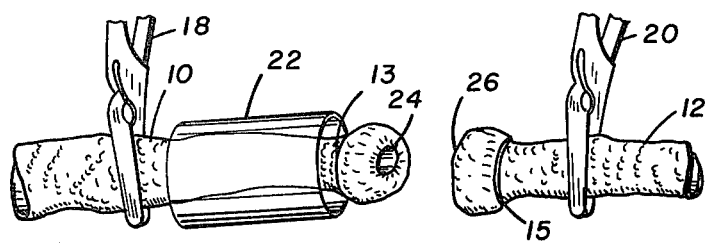
Figure 1C:
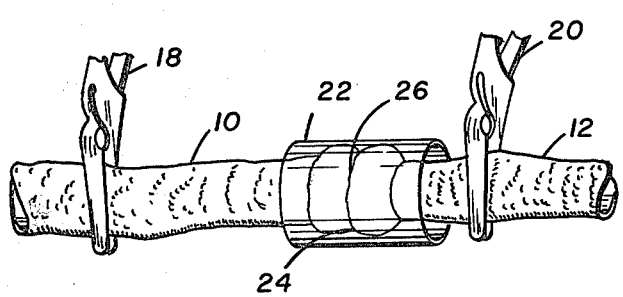
Figure 1D:
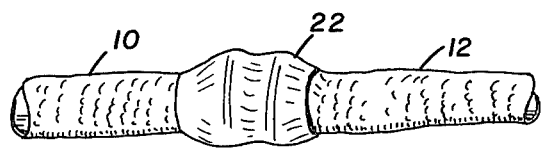

FIG. 1B shows the ends of members 10, 12 everted over ferrules 14, 16 respectively and shrinkable sleeve 22 placed around member 10. It is noted that shrinkable sleeve 22 may be initially placed around either of members 10, 12. The eversion of ends 13, 15 of members 10, 12 respectively results in everted ends 24, 26 on members 10, 12 respectively. FIG. 1C shows everted ends 24, 26 placed in an end-to-end anastomotic relationship and shrinkable sleeve 22 placed in a position ready to be shrunk. FIG. 1D shows members 10, 12 anastomosed with shrinkable sleeve 22 shrunken.

Figure 2A:
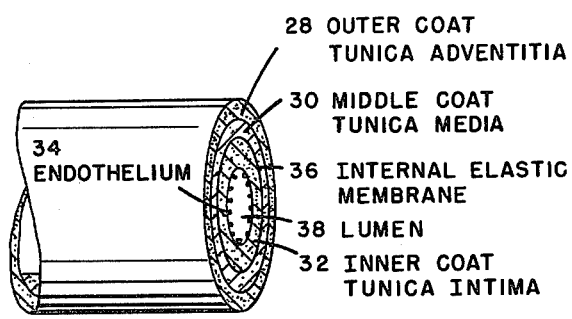
FIG. 2A is a view of a vascular vessel with a cross sectional view showing its structure.

FIG. 2A shows a blood vessel with a cross sectional view showing the layers that make up a blood vessel. The blood vessel is made up of three coats: an outer coat 28 or tunica adventitia consisting of a strong fibrous sheath; the middle coat 30 or tunica media consisting of muscular fibers; and the inner coat 32 or tunica intima consisting of a layer of elastic tissue lined with plate-like endothelial cells 34. Between the middle coat 30 and the inner coat 32 there is an internal elastic membrane 36. The hollow interior wherein the blood flows is termed the lumen 38. As is known in the surgical art, to insure a successful anastomosis of a vascular vessel it is imperative that the inner coats 32 of the two members be brought into contact to promote healing and to have a continuous layer of endothelial cells 34. This lessens the possibility of the formation of thrombi and the resulting occlusion of the anastomosed vessel which, as can be appreciated, could result in death or loss of limb to the patient. Another potential problem area is necrosis which can be caused by a portion of the vessel being anastomosed being pinched or being depleted from a blood supply. The necrotic area that results is a potential source of infection or a potential weak area that could cause the anastomosed vessel to fail, again with possible disastrous results. It is here emphasized that although the procedures described herein are described in relation to blood vessels the same techniques can be employed to the joining of any two tubular members with slight modifications to the procedure taught by the present invention which would be obvious to one of ordinary skill in the art.

Figure 2B:
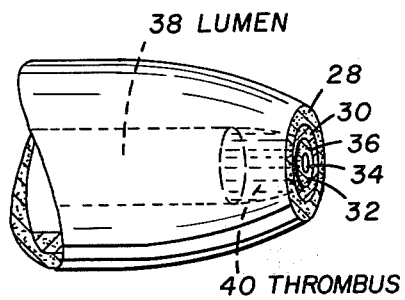
FIG. 2B is a view of a portion of the vessel shown in FIG. 2A showing its reaction to be severed.

Returning now to the drawings, FIG. 2B is a pictorial representation of the reaction that occurs when a blood vessel is severed. Upon severence middle layer 30 immediately constricts causing the lumen 38 at the point of severence to become as small as possible to prevent a large loss of blood by allowing a blood clot or thrombus 40 to be more easily formed. During an anastomotic procedure it is necessary to remove the thrombi formed in the two members being anastomosed. The methods of removing thrombi are well known in the surgical art.

Figure 2C:
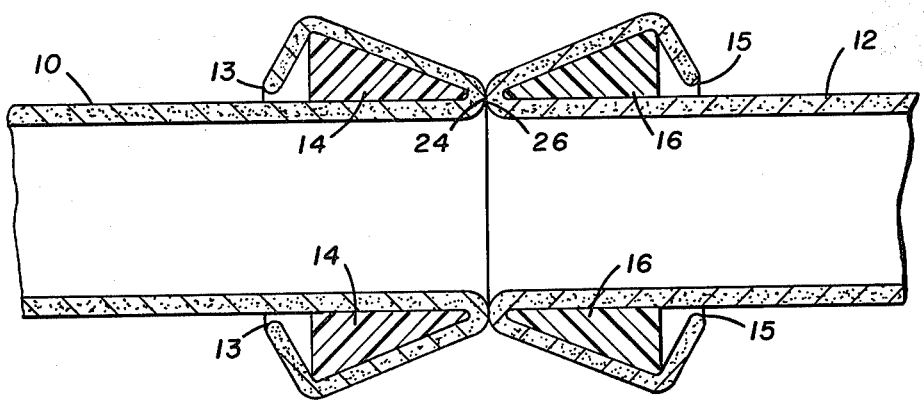
FIG. 2C is a cross sectional view of two portions of a severed vessel each of which have been everted over a ferrule and placed in an anastomotic relationship.
Figure 2D:
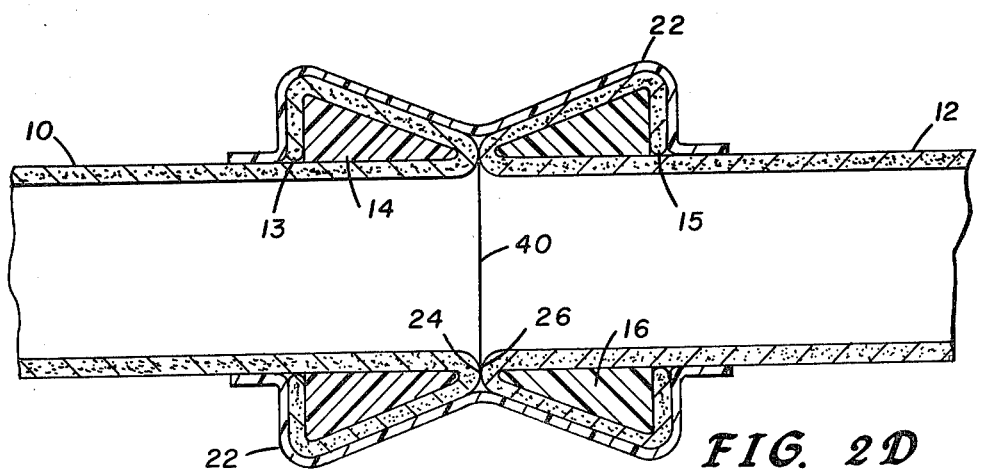
FIG. 2D is a cross sectional view of the two portions shown in FIG. 2C with the shrinkable sleeve shrunken as taught by the present invention.

FIG. 2C is a cross sectional view of two members 10, 12 with end 13 of member 10 everted over ferrule 14 and end 15 of member 12 everted over ferrule 16. The resulting everted ends 24, 26 are shown placed in an end-to-end anastomotic relationship. As can be appreciated, the technique as taught by the present invention results in the inner layers placed in a firm, intimate anastomotic relationship as required for successful anastomosis. As also can be appreciated, the selection of proper size ferrules 14, 16 ensures that the resulting anastomotic region is not constricted. As is well known a constriction (reduced diameter) in an anastomosed blood vessel has a tendency to encourage formation of thrombi. Additionally, because the technique as taught by the present invention is sutureless there is no possibiliy that a misplaced suture penetrating the lumen can cause formation of thrombi. FIG. 2D is a cross sectional view of the two members 10, 12 shown in FIG. 26 with shrinkable sleeve 22 shrunken over the anastomosis region. The shrunken shrinkable sleeve firmly holds ends 13, 15 against ferrules 14, 16 respectively. As will be explained in more detail below shrinkable sleeve 22 can be selected to shrink in the radial direction and in the longitudinal direction. As can be appreciated from FIG. 2D the radial direction shrinkage causes the shrinkable sleeve 22 to firmly hold the portions of members 10, 12 between ends 13, 15 and everted ends 24, 26 against ferrules 14, 16 respectively. The longitudinal shrinkage causes firm intimate contact between everted ends 24, 26 and thereby junction 40 between members 10, 12 will not allow leakage of fluid from the vessels.

Figure 3A:
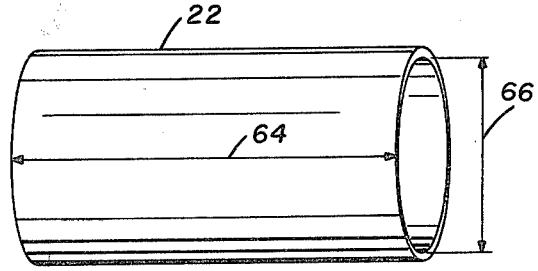
FIGS. 3A & 3B are two embodiments of the shrinkable sleeve in an unshrunken state.
Figure 3B:
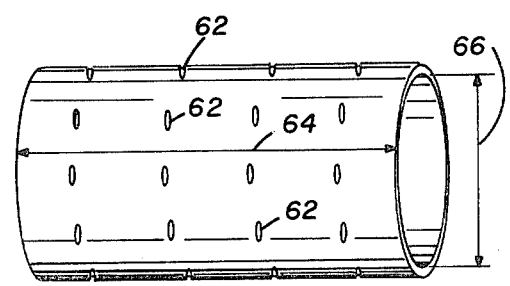

FIG. 3A is an illustration of the shrinkable sleeve in its unshrunken state. The sleeve may be manufactured in various diameters and in a continuous roll. The surgeon then selects the sleeve with a diameter larger than the members to be anastomosed and large enough to easily fit over the ends everted over the ferrules. The surgeon then cuts the sleeve to the correct length. The correct length is selected so that each end of the shrinkable sleeve extends approximately 15% of its length beyond each everted end and the underlying ferrule. This allows a longitudinal shrinkage of approximately 15% so that the shrinkable sleeve extends slightly beyond each everted end and the underlying ferrule after being shrunk. FIG. 3B illustrates another embodiment of a shrinkable sleeve. In this embodiment the sleeve is manufactured with small holes 62 through the walls of the sleeve 22 to allow body fluids to reach the members underlying the sleeve 22. It may be advantageous and desirable in some applications to have a perforated or cribreformed sleeve. Referring to both FIGS. 3A and 3B the length 64 is selectable by the surgeon as discussed above and the sleeves are manufactured with various diameters represented at 66.

Heat shrinkable tubing is currently being used in the electronics industry to protect and encapsulate electronics connectors and components. Silicone rubber, Teflon, polyvinyl chloride (PVC), polyethylene and neoprene are materials currently being used. The degree of shrinkage is established during the manufacturing process. Radial shrink ratios, for these materials, range from 2:1 to 10:1 and the longitudinal shrinkages range from 5 to 15 percent. However none of the commercially available heat shrinkable materials possess all of the properties required for anastomosis procedure as taught by the present invention. For example, neoprene can undergo shrinking at a low temperature (approximately 140° F.) but it is not biocompatible; Teflon is implantable, but high temperatures are needed to cause shrinking.

A successful heat shrinkable polymer for the anastomosis procedure as taught by the present invention must have good in vivo stability; possess a low crystalline melt point [approximately 50° C. (122° F.) to 70° C.(158°)] to minimize damage to biological tissue during the application of heat; form crosslinks rather than degrade when irradiated; and have at least a moderate tensile strength. Additional desired qualities, but not critical qualities are that the sleeve remain somewhat flexible in vivo and be clear or transparent to allow the surgeon to verify installation during and after the installation.

The development of a heat shrinkable material is accomplished by causing certain polymers to form crosslinks between the long molecular chains in the polymer. Causing a polymer to form crosslinks can be done by a chemical reagent or by irradiation. However, some of the reagents used in the chemical process leave toxic residues. The preferred method of forming a biocompatible heat shrinkable polymer is by irradiation.

The method of producing a heat shrinkable tubing by irradiation is well known in the art. The radiation processing generally used is limited to two types of ionizing radiation: cobalt-60 gammas (approximately 1.25 MeV) and electrons with energies in the range 0.2–10 MeV. The production of a heat shrinkable polymer is accomplished by irradiating a suitable polymer with a dose of radiation between 5–20 Mrad to produce crosslinks in the polymer, heating the polymer to the crystalline melting temperature, stretching and then quickly cooling the polymer in the stretched configuration. The polymer remains in the stretched configuration until heated to at or above the melting point of the crystalline structure at which time the crosslinks cause a rubber like contraction to the original form.

The crosslinks in a heat shrinkable polymer are not affected by the application of heat whereas the crystal structure will melt if raised to the proper temperature. The tension in the crosslinks is sufficient to cause the polymer to shrink. The final diameter of the sleeve and the level of compression produced by the sleeve are selected so that the installed sleeve will not be too tightly drawn causing necrotic areas or too loose permitting escessive bleeding and union failure.

Specific polymers that have the requisite properties for a biocompatible shrinkable sleeve may be found in the following generic classes of polymers; polyethylenes, polypropylenes, polyesters and polyoxides. The best mode known at the present time is either polyethylene oxide or polyethylene adipate. Other materials from the generic classes listed above may or may not be better suited for the heat shrinkable sleeve as taught by the present invention. As can be appreciated, the selection of materials to be used in the human body must be done with especial care and caution and is a long term process.

Returning now to the figures and specifically to FIGS. 1A–1D which were discussed above with specific reference to a vascular application. The present invention comprehends the application to an anastomotic procedure wherein one of the members being anastomosed is a prosthesis. For example, second member 12 in FIGS. 1A–1D or second member 12 in FIGS. 2C and 2D may be a prosthesis. As is well known in the art the clinical success or prosthetic grafts as they are presently performed are largely dependent on the methods of suturing. In other words major problems are caused by the suturing process. If sutures are improperly made interfaces result which causes turbulent flow and clotting. If the sutures are too tight nectoric areas result. If the sutures are too loose the interface leaks or may be a cause of early failure. Experience has shown that with prosthetic grafts in humans, a strong fibrous bond does not characteristically develop between the graft and the vessel, and the union is dependent upon the strength of the anastomotic suture. The prostheses, depending upon the type of material, vary in the ability to hold sutures. The present invention provides a method wherein no sutures have to be taken either in the existing vessel or the prosthesis.

Figure 4A:
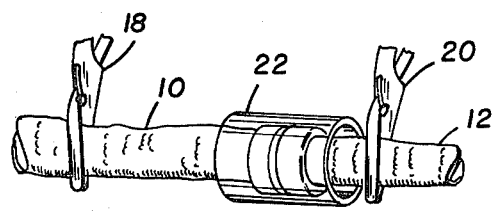
FIGS. 4A–4D are sequential pictorials of the method of applying heat to the heat shrinkable sleeve in the anastomosis technique as taught by the present invention.
Figure 5A:
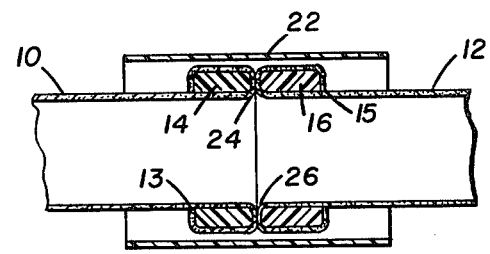
FIGS. 5A–5D are sequential cross sectional views, corresponding to FIGS. 4A–4D respectively, showing the relationship of the two portions being anastomosed, the ferrules placed on the two portions and the shrinkable sleeve.
Figure 4B:
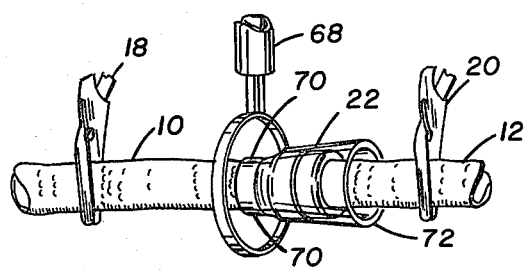
Figure 5B:
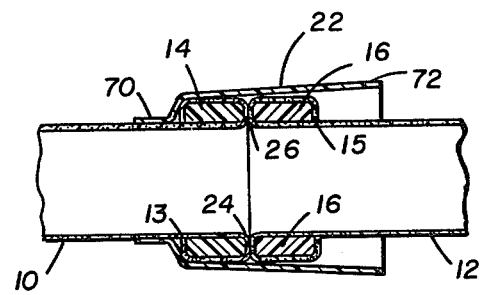
Figure 4C:
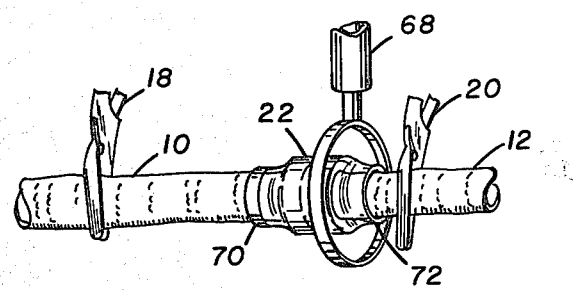
Figure 5C:
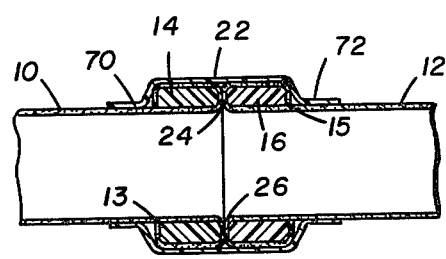
Figure 4D:
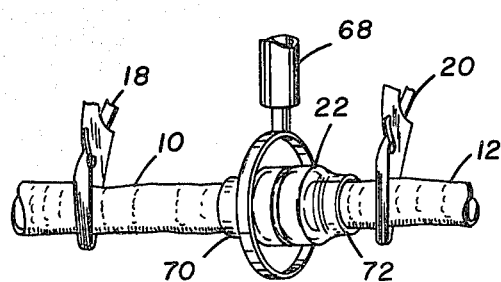
Figure 5D:
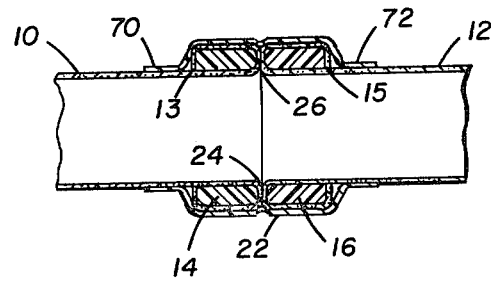

Referring to FIGS. 4A–4D and FIGS. 5A–5D the methods of applying heat to the heat shrinkable sleeve will now be explained. FIGS. 5A–5D are sequential cross sectional views of the junction shown in FIGS. 4A–4D respectively. FIG. 4A shows first member 10 and second member 12 placed in an end-to-end anastomotic relationship with heat shrinkable sleeve 22 positioned ready to be shrunk. FIG. 5A is a cross sectional view of the junction shown in FIG. 4A. FIG. 4B shows a heating wand 68 disposed around a first end 70 of shrinkable sleeve 22. The details of heating wand 68 will be discussed below. End 70 shrinks principally in a radial direction and holds end 13 of first member 10 firmly around ferrule 14 as shown in FIG. 5B. FIG. 5C shows heating wand 68 disposed around a second end 72 of shrinkable sleeve 22. End 72 shrinks principally in a radial direction and holds end 15 of second member 12 firmly around ferrule 16 as shown in FIG. 5C. FIG. 4D shows heating wand 68 disposed around the center of sleeve 22. The center of sleeve shrinks in a radial direction around ferrules 14 and 16 and forms a tight bond around the anastomosis junction. In addition, sleeve 22 shrinks in a longitudinal direction causing ends 70, 72 of sleeve 22 to be drawn towards the center of the anastomotic junction causing everted ends 24, 26 to form a tight leakproof bond, shown in FIG. 5D.

Figure 6:
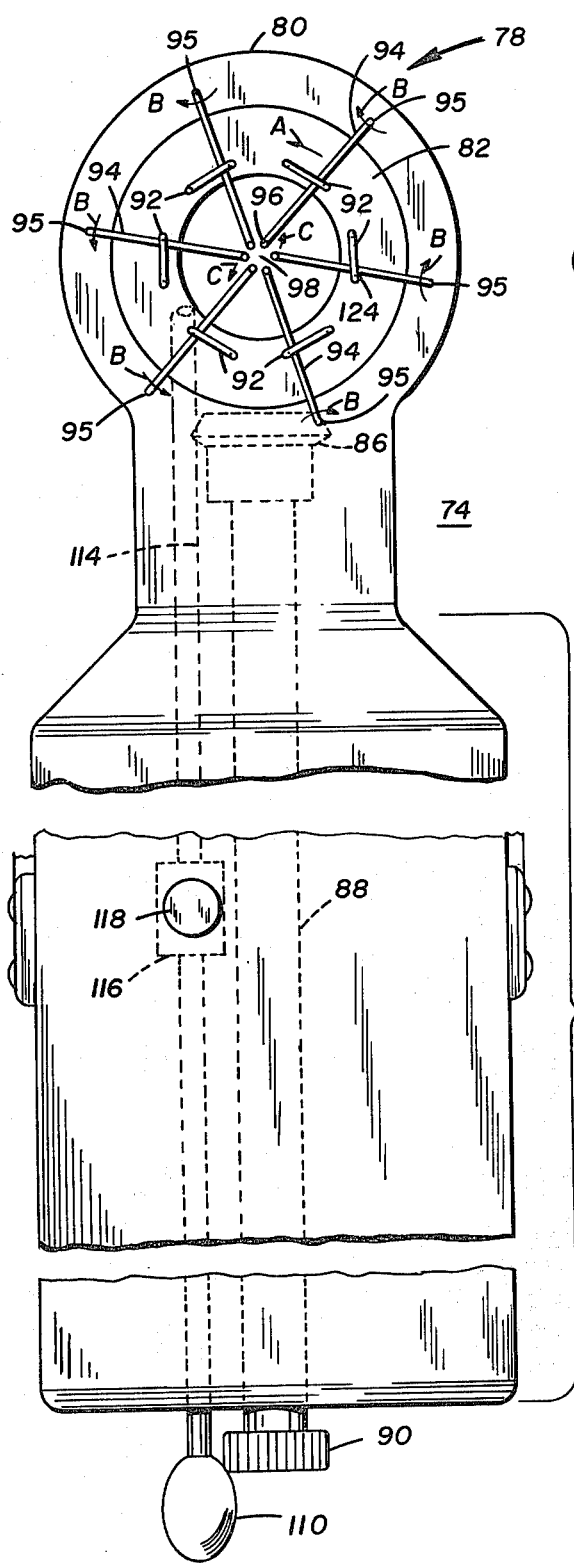
FIG. 6 is a plan view of the everting tool employed in the anastomosis technique as taught by the present invention.
Figure 7:
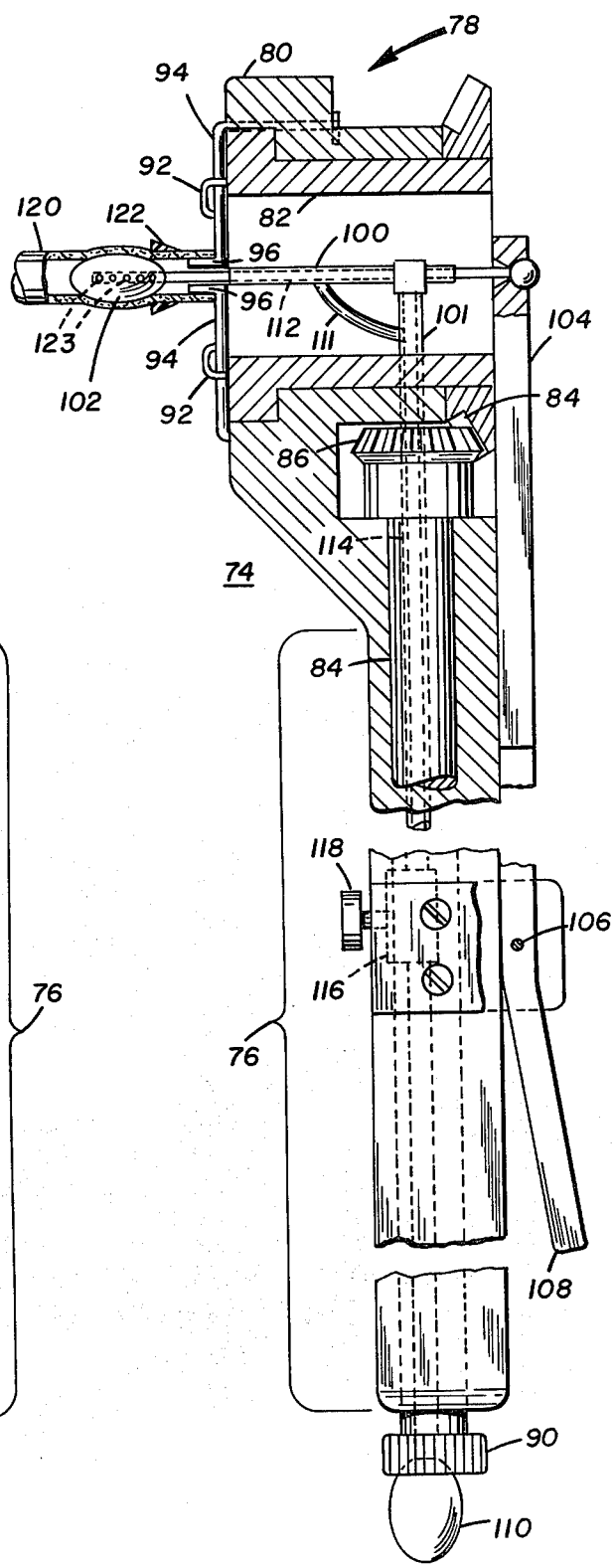
FIG. 7 is a side view of the everting tool shown in FIG. 6 with a portion of a tubular member in position for the initiation of the everting process as taught by the present invention.

Referring now to FIGS. 7, 8 an embodiment of an everting tool will now be discussed. The sutureless anastomotic procedure taught by the present invention requires an efficient method of everting the ends of the tubular members being anastomosed over the ferrules placed on the ends. The everting means must have a method for holding the ferrule stationary while the end of the member being anastomosed is everted over the ferrule. Additionally, the everting means must have a method of expanding the end and folding the end over the ferrule. FIGS. 6, 7 illustrate an embodiment of an everting tool 74 and comprises generally a handle portion 76 and a head portion 78. Head portion 78 further comprises a stationary section 80 attached to handle 76. A rotatable section 82 is disposed within stationary section 80 and has a gear face 84 (FIG. 7) disposed thereon. Gear face 84 meshes with gear 86 which is attached to rotatable shaft 88 which extends through handle 76 and is attached to knob 90. Rotatable section 82 has six staple shaped members 92 disposed thereon. Staple members 92 extend above the surface of rotatable section 82. Six rotatable levers 94 are rotatably attached to stationary section 80 at pivot points 95 and extend through the space between staple members 92 and rotatable section 82. Rotatable levers 94 are disposed towards the center of head portion 78 and terminate with outwardly pointing prongs 96. The prongs 96 when in a closed position, as shown in FIGS. 6, 7 define a circular space 98 therebetween. The everting tool further comprises a slidable shaft 100 with an inflatable balloon 102 (shown inflated in FIG. 7) attached to one end thereof. Inflatable balloon 102 and a portion of slidable shaft 100 extend through circular space 98 defined by prongs 96. Slidable shaft 100 is held in place by support member 101 and is slidable therethrough. The other end of slidable shaft 100 is pivotably attached to lever 104. Lever 104 extends along handle 76, is pivoted at pivot 106 and bends outwardly from handle 76 and comprises a lever handle 108. Inflatable balloon 102 communicates with a fluid supply comprising a pressurization bulb 110 via passageway 112 within slidable shaft 100, flexible tube 111 and passageway 114 within support member 101 and handle 76. Passageway 114 passes through a controllable check valve 116 controlled by knob 118. Check valve 116 can be opened to allow fluid in inflatable balloon 102 to be bled off.

The operation of everting tool 74 will now be explained referring to FIGS. 6 and 7. Inflatable balloon 102 and a portion of slidable shaft 100 are inserted by the surgeon into the lumen of a vessel 120 or other member to be anastomosed. A ferrule 122 has been previously disposed on vessel 120. At the same time prongs 96 are inserted into vessel 120 until the end of vessel 120 is flush against rotatable levers 94. The surgeon inflates inflatable balloon 102 by squeezing pressurization bulb 110 which forces fluid through passageway 114 and check valve 116, through passageway 112, flexible tube 111 and into inflatable balloon 102 via holes 123 in slidable shaft 100. Inflatable balloon 102 is inflated until the walls of vessel 120 are pushed outwardly a sufficient distance to prevent ferrule 122 from sliding along vessel 120. The amount of vessel wall extension caused by inflation of balloon 102 is monitored visually by the surgeon. During this step of the procedure, knob 118 is in a closed position, i.e., to prevent fluid from bleeding out of balloon 102. The surgeon then rotates knob 90 causing shaft 88 to rotate, causing gear 86 to rotate, causing gear face 84 to rotate and thus rotatable section 82 is caused to rotate. Referring to FIG. 6, if rotatable section 82 is caused to rotate in the direction of arrow A, rotatable levers 94 will pivot around pivot points 95 in the direction of arrow B. This motion is caused by staple 92 rotating with rotatable section 82 and bearing against rotatable levers 94 at a point indicated by 124 of staples 92. The rotation of levers 94 causes prongs 96 to move in the direction of arrow C. The reaction of all the prongs define an iris-diaphragm effect causing the end of vessel 120 to expand radially. The remaining steps of the procedure will be explained by referring to FIGS. 9A-9E which are sequential pictorials illustrating the complete eversion procedure.

FIG. 8A shows vessel 120 with ferrule 122 disposed thereon and everting tool head 78 with inflatable balloon 102 deflated and prongs 96 in a closed position. FIG. 8B is a view of the balloon 102 inserted and inflated in vessel 120. FIG. 8C shows prongs 96 in the open position and the end of vessel 120 being radially expanded. Note that the expansion of the walls of vessel 120 by balloon 102 prevents ferrule 122 from sliding out of position. It is noted that the amount of radial expansion of prongs 96 is controllable by the surgeon by controlling the degree of rotation of knob 90 (FIGS. 6, 7) and is dependent upon the original size of the vessel being anastomosed. FIG. 8D is a view of the ends of vessel 120 beginning to be folded over ferrule 122. The folding over is caused by the surgeon causing lever 102 to move outward which causes slidable shaft 100, balloon 102 and the vessel 120 to be drawn towards the everting tool in the direction of arrow D. This causes prongs 96 to fold the end of vessel 120 over the outer periphery of ferrule 122. Lever 104 is caused to move outward by the surgeon depressing lever handle 108 (FIG. 7). FIG. 8E shows the eversion procedure completed, i.e., the end of vessel 120 completely folded over ferrule 122 and the balloon 102 ready to be withdrawn from the vessel 120. This is accomplished by the surgeon further depressing lever handle 108 (FIG. 7) causing lever 104 to move further outward causing slidable shaft 100 and the deflated balloon 102 to be withdrawn from the vessel. It is to be appreciated that prongs 96 press against vessel 120 over ferrule 122 allowing the deflated balloon to be withdrawn. Also, it is to be appreciated that the balloon is caused to be deflated by the surgeon opening knob 118 (FIG. 7) which opens check valve 116 (FIG. 7) allowing fluid to bleed out of balloon 102 via passageway 112 in slidable shaft 100 and passageway 114 in support 101 and handle 76.

Figure 9A:
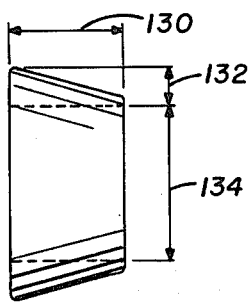
FIGS. 9A–9B show two embodiments of the ferrules as taught by the present invention.
Figure 9B:
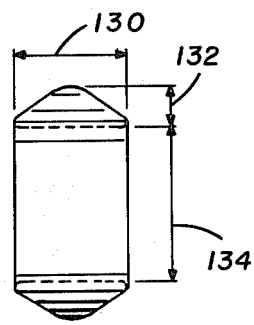
Figure 9C:
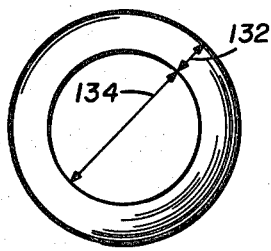
FIG. 9C shows a plan view of a ferrule.

Referring now to FIGS. 9A-9B there are shown in cross section two embodiments of ferrules suitable for the procedure as taught by the present invention. FIG. 9C is a plan view of a ferrule. The preferred embodiment is a ferrule which is rigid or semi-rigid to provide support for the vessel and to prevent the vessel from collapsing when the shrinkable tubing is shrunk. The ferrules serve to open, and maintain open, the occluded ends of the vessel. Because the ferrules do not contact the blood within the vessel the problem of the formation of thrombi is avoided and the material selection is based upon the following factors: the ferrules should not induce an inflammatory reaction, should be non-toxic and should be dimensionally stable. If the application in which the ferrules are to be used provides natural healing such that sufficient vessel strength is developed then in vivo degradable materials such as collagen (treated natural tissue) or polyglycolate may be used. If long-term, stable ferrules are desired then a polypropylene or polyethylene material is desirable. The preferred shape is shown in FIG. 9B wherein the external diameter is greatest in the center and tapers towards the ends of the ferrule. This shape eases vessel eversion and helps to keep the vessel wall in place after the sleeve is installed and shrunk. It is anticipated that the ferrules will be manufactured in several sizes, however, nominal dimensions are as follows: the dimension indicated at 130 is approximately 0.10 inches, the dimension indicated at 132 is approximately 0.03 inches and the dimension indicated at 134 is between approximately 0.12 inches and 0.22 inches.

Figure 10:
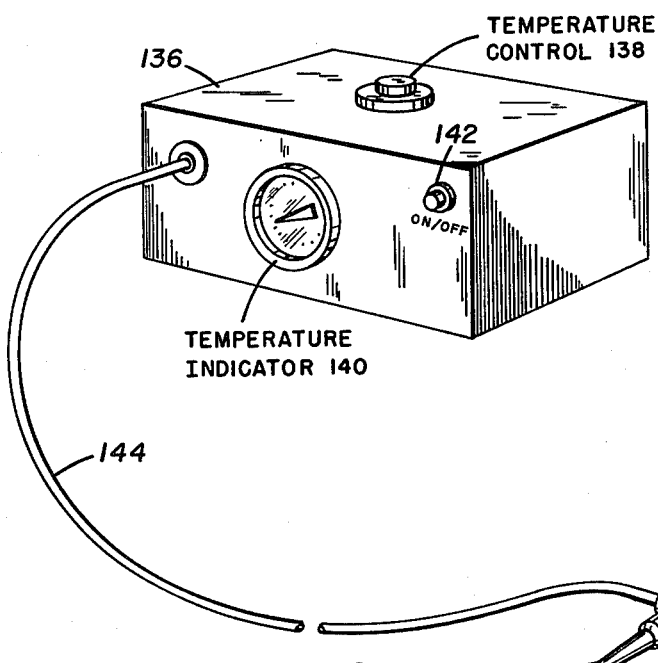
FIG. 10 is a pictorial of the heating means as taught by the present invention.
Figure 11:
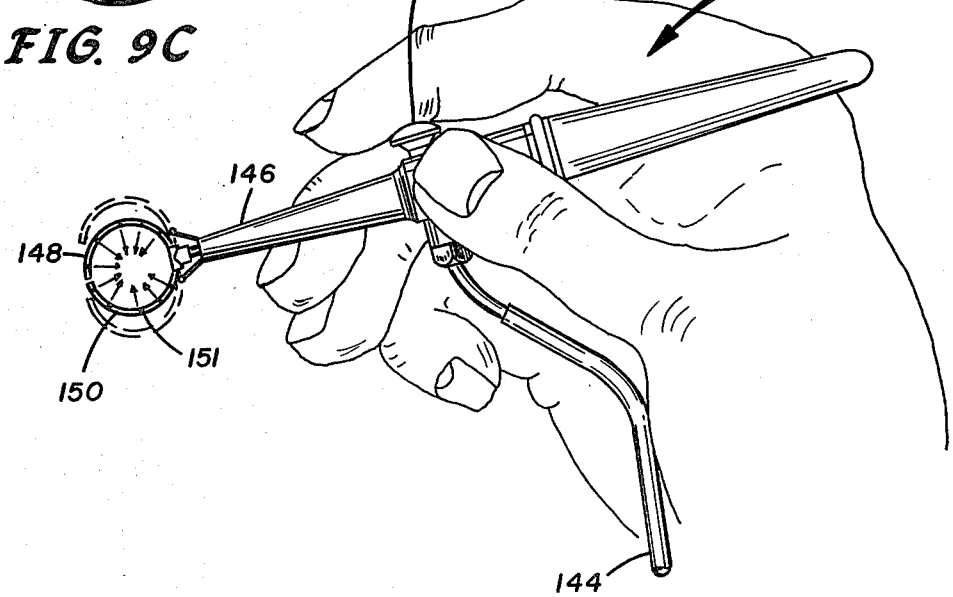
FIG. 11 is a pictorial of the heating means wand and its method of use.

Referring now to FIG. 10 there is shown a pictorial representation of the heating means for applying heat to the heat shrinkable sleeve. The heating control indicated generally at 136 comprises a source of heat which may be an electrical coil and fan (not shown) a temperature selector control 138, a temperature indicator 140, an on/off control 142 and a communication means 144 which may be a tubular member to transport hot air to a heating wand 68. Referring now to FIG. 11 the heating wand 68 is shown in more detail. The preferred embodiment comprises a handle 146, an upper jaw 148 and a lower jaw 150 which are closable to encircle the vessel being anastomosed, and a dual finger control 152 to allow the surgeon to control whether the heat is on or off and to control the opening and closing of jaws 148 and 150. Heat is supplied to the sleeve by hot air flowing from heating means 136 via tube 144 through handle 146 to jaws 148, 150 and then through outlets 151 disposed radially around jaws 148, 150. The flow of air is depicted by the arrows in FIG. 11. The operation is as follows: the wand with jaws 148, 150 in the open position, indicated by dashed lines in FIG. 12, is placed around the portion of the sleeve to be shrunk, the jaws 148, 150 are closed by the surgeon with dual control 152 and hot air is caused by the surgeon operating dual control 152 to be directed onto the sleeve to be shrunk.

While the invention has been described with reference to the accompanying drawings, it is to be clearly understood that the invention is not to be limited to the particular details shown therein, as various modifications, adaptations and alterations are within the scope of the following claims.

What I claim is:

1. A means for performing sutureless surgical anastomosis between a first tubular member and a second tubular member, comprising:
   a first ferrule placed around an end of said first member;
   a second ferrule placed around an end of said second member;
   means for everting said ends of said first and second members over said first and second ferrules, respectively;
   a shrinkable sleeve placed around said first and second members;
   means for shrinking said shrinkable sleeve wherein said first and second ferrules and said shrinkable sleeve cooperate to hold said first and second members in an anastomotic relationship.

2. A means, as recited in claim 1, wherein said first member comprises a first portion of a severed vessel and said second member comprises a second portion of said severed vessel.

3. A means, as recited in claim 1, wherein said first member comprises a severed vessel and said second member comprises a replacement vessel removed from the same or another part of a body.

4. A means, as recited in claim 1, wherein said first member comprises a severed vessel and said second member comprises a prosthesis.

5. A means as recited in claim 2, 3 or 4 wherein said means for everting comprises:
   means for expanding each of said ends of said first and second members; and
   means for folding said expanded ends of said first and second members over said first and second ferrules, respectively, whereby said folded ends extend beyond each of said ferrules, respectively.

6. A means, as recited in claim 5, wherein said means for everting further comprises means for maintaining said first and second members stationary relative to said first and second ferrules, respectively.

7. A means, as recited in claim 6, wherein said means for maintaining said first and second members stationary comprises:
   an inflatable balloon;
   means for alternately inserting said inflatable balloon into said end of said first and second member;
   means for inflating said inflatable balloon whereby said first and second member is expanded by said inflated balloon and is held securely against said first and second ferrule, respectively;
   means for deflating said balloon; and
   means for withdrawing said balloon.

8. A means, as recited in claim 7, wherein said shrinkable sleeve comprises a heat shrinkable sleeve and further comprising means for applying heat to aid heat shrinkable sleeve.

9. A means, as recited in claim 8, wherein said heat shrinkable sleeve is fabricated with a selectable radial dimension in an unshrunken state selected to be larger than said members to be anastomosed and with a selectable longitudinal dimension selected to extend beyond said first and second ferrules when in a shrunken state.

10. A means, as recited in claim 9, wherein said heat shrinkable sleeve is selectively shrinkable in a radial direction.

11. A means, as recited in claim 10, wherein said heat shrinkable sleeve is selectively shrinkable in a longitudinal direction.

12. A means, as recited in claim 11, wherein said means for applying heat comprises means for subjecting said heat shrinkable sleeve to a selectable temperature change, said temperature change being from a first temperature to a second temperature wherein said second temperature is greater than said first temperature.

13. A means, as recited in claim 12, wherein said heat shrinkable sleeve is fabricated from a biocompatible material which shrinks upon an application of heat at said second temperature selected to minimize damage to biological tissue.

14. A means, as recited in claim 13, wherein said second temperature is selected to be in the range of 50° C. to 70° C.

15. A means, as recited in claim 14, wherein said heat shrinkable sleeve is fabricated from a heat shrinkable polymer.

16. A means, as recited in claim 15, wherein said heat shrinkable sleeve is fabricated from a material selected from a group comprised of polyethylene, polypropylene, polyester and polyoxide.

17. A means, as recited in claim 15, wherein said heat shrinkable sleeve is fabricated with a smooth continuous wall.

18. A means, as recited in claim 15, wherein said heat shrinkable sleeve is fabricated with a cribreformed wall.

19. A means, as recited in claim 15, wherein said ferrules are fabricated from a biostable rigid material.

20. A means, as recited in claim 19, wherein said ferrules are fabricated from a material selected from a group comprising polypropylene and polyethylene.

21. A means, as recited in claim 15, wherein said ferrules are fabricated from an in vivo degradable material.

22. A means, as recited in claim 21, wherein said ferrules are fabricated from a material selected from a group comprising collagen and polyglycolate.

23. A method for performing sutureless surgical anastomosis between a first tubular member and a second tubular member comprising the steps of:
   placing a first ferrule around an end of said first member;
   placing a second ferrule around an end of said second member;
   everting said end of said first member over said first ferrule;
   everting said end of said second member over said second ferrule;
   placing a shrinkable sleeve around said first and second members to be anastomosed;

placing said everted ends of said first and second members in an anastomotic relationship; and shrinking said shrinkable sleeve around said first and second members whereby the shrunken shrinkable sleeve securely engages and maintains said first and second members in said anastomotic relationship.

24. A method, as recited in claim 23, wherein said first member comprises a severed vessel and wherein said second member comprises a replacement vessel comprising a portion of a vessel removed from the same or another part of a body.

25. A method, as recited in claim 23, wherein said first member comprises a severed vessel and wherein said second member comprises a prosthesis.

26. A method, as recited in claim 23 wherein:

said first and second members comprise a severed biological tubular member comprising a connecting tissue sheath enclosing further biological members;

said step of preparing said first and second members for anastomosis is accomplished by placing said further biological members in said anastomotic relationship; and said shrunken shrinkable sleeve securely engages and maintains said connecting tissue sheath in said anastomotic relationship.

27. A method, as recited in claim 26, further comprising the step of removing thrombi and other foreign material from said ends.

28. A method, as recited in claim 27, wherein the steps of everting include the steps of:

expanding said end of said first member;

folding said expanded end of said first member over said first ferrule whereby said everted end extends beyond said first ferrule;

expanding said end of said second member; and folding said expanded end of said second member over said second ferrule whereby said everted end extends beyond said second ferrule.

29. A method, as recited in claim 28, wherein said steps of everting further includes the step of maintaining said first and second members stationary relative to said first and second ferrules respectively during said steps of enlarging said ends and folding said enlarged ends.

30. A method, as recited in claim 29, wherein said step of maintaining said first and second members stationary includes the steps of:

inserting an inflatable balloon into said end of said first member;

inflating said balloon whereby said first member is held securely against said first ferrule during said step of everting said first member;

deflating and withdrawing said balloon from said first member;

inserting said inflatable balloon into said end of said second member;

inflating said balloon whereby said second member is held securely against said second ferrule during said step of everting said second member; and deflating and withdrawing said balloon from said second member.

31. A method, as recited in claim 24 further comprising the step of removing thrombi and other foreign material from said ends of said severed vessel and said replacement vessel.

32. A method, as recited in claim 31, wherein the steps of everting include the steps of:

expanding said end of said severed vessel;

folding said expanded end of said severed vessel over said first ferrule whereby said everted ends extends beyond said first ferrule;

expanding said end of said replacement vessel; and folding said expanded end of said replacement vessel over said second ferrule whereby said everted end extends beyond said second ferrule.

33. A method, as recited in claim 32, wherein said steps of everting further includes the step of maintaining said severed vessel and said replacement vessel stationary relative to said first and second ferrules respectively during said steps of enlarging said ends and folding said enlarged ends.

34. A method, as recited in claim 33, wherein said step of maintaining said severed vessel and replacement vessel stationary includes the steps of:

inserting an inflatable balloon into said end of said severed vessel;

inflating said balloon whereby said severed vessel is held securely against said first ferrule during said step of everting said severed vessel;

deflating and withdrawing said balloon from said severed vessel;

inserting said inflatable balloon into said end of said replacement vessel;

inflating said balloon whereby said replacement vessel is held securely against said second ferrule during said step of everting said replacement vessel; and deflating and withdrawing said balloon from said replacement vessel.

35. A method, as recited in claim 25, further comprising the step of removing thrombi and other foreign material from said end of said severed vessel.

36. A method, as recited in claim 35, wherein the steps of everting include the steps of:

expanding said end of said severed vessel;

folding said expanded end of said severed vessel over said first ferrule whereby said everted and extends beyond said first ferrule;

expanding said end of said prosthesis;

folding said expanded end of said prosthesis over said second ferrule whereby said everted end extends beyond said second ferrule.

37. A method, as recited in claim 36, wherein said steps of everting further includes the step of maintaining said severed vessel and said prosthesis stationary relative to said first and second ferrules respectively during said steps of enlarging said ends and folding said enlarged ends.

38. A method, as recited in claim 37, wherein said step of maintaining said severed vessel and said prosthesis stationary includes the steps of:

inserting an inflatable balloon into said end of said severed vessel;

inflating said balloon whereby said severed vessel is held securely against said first ferrule during said step of everting said severed vessel;

deflating and withdrawing said balloon from said severed vessel;

inserting said inflatable balloon into said end of said prosthesis;

inflating said balloon whereby said prosthesis is held securely against said second ferrule during said step of everting said prosthesis; and deflating and withdrawing said balloon from said prosthesis.

39. A method, as recited in claim 23 wherein said shrinkable sleeve comprises a heat shrinkable sleeve and wherein said step of shrinking is accomplished by a step of applying heat to said heat shrinkable sleeve.

40. A method, as recited in claim 39, wherein said shrinkable sleeve comprises a heat shrinkable sleeve with a selectable radial dimension in an unshrunken state selected to be larger than said members to be anastomosed and with a selectable longitudinal dimension selected to extend beyond said first ferrule and said second ferrule when in a shrunken state.

41. A method, as recited in claim 40, wherein said heat shrinkable sleeve is selectively shrinkable in a radial direction.

42. A method, as recited in claim 41, wherein said heat shrinkable sleeve is selectively shrinkable in a longitudinal direction.

43. A method, as recited in claim 42, wherein the step of applying heat to said heat shrinkable sleeve includes the steps of:
applying heat to a first end of said heat shrinkable sleeve whereby said first end of said heat shrinkable sleeve shrinks in a radial direction and securely holds said folded end of said first member around said first ferrule;
applying heat to a second end of said heat shrinkable sleeve whereby said second end of said heat shrinkable sleeve shrinks in a radial direction and securely holds said folded end of said second member around said second ferrule; and
applying heat to a portion of said heat shrinkable tubing between said first end and said second end whereby said heat shrinkable sleeve shrinks in a radial direction and a longitudinal direction whereby said everted ends of said first and second members are brought into and maintained in a tight anastomotic relationship.

44. A method, as recited in claim 43, wherein the steps of applying heat are accomplished by subjecting said heat shrinkable sleeve to a selectable temperature change, said temperature change being from a first temperature to a second temperature wherein said second temperature is greater than said first temperature.

45. A method, as recited in claim 44, wherein said heat shrinkable sleeve is fabricated from a biocompatible material which shrinks upon an application of heat at said second temperature selected to minimize damage to biological tissue.

46. A method, as recited in claim 45, wherein said second temperature is selected to be in the range of 50° C. to 70° C.

47. A method, as recited in claim 46, wherein said heat shrinkable sleeve is fabricated from a heat shrinkable polymer.

48. A method, as recited in claim 47, wherein said heat shrinkable sleeve is fabricated from a material selected from a group comprised of polyethylene, polypropylene, polyester and polyoxide.

49. A method, as recited in claim 47, wherein said heat shrinkable sleeve is fabricated with a smooth continuous wall.

50. A method, as recited in claim 47, wherein said heat shrinkable sleeve is fabricated with a cribreformed wall.

51. A method, as recited in claim 47, wherein said ferrules are fabricated from a biostable rigid material.

52. A method, as recited in claim 51, wherein said ferrules are fabricated from a material selected from a group comprising polypropylene and polyethylene.

53. A method, as recited in claim 47, wherein said ferrules are fabricated from an in vivo degradable material.

54. A method, as recited in claim 53, wherein said ferrules are fabricated from a material selected from a group comprising collagen and polyglycolate.

* * * * *